United States Patent [19]

Savides et al.

[11] Patent Number: 4,536,596

[45] Date of Patent: Aug. 20, 1985

[54] EXTRACTION OF AMINO ACIDS FROM AQUEOUS SOLUTION WITH DITHIOPHOSPHINATES

[75] Inventors: Christos Savides, Fairfield; John H. Bright, Norwalk, both of Conn.

[73] Assignee: American Cyanamid Company, Stamford, Conn.

[21] Appl. No.: 609,947

[22] Filed: May 14, 1984

[51] Int. Cl.³ .............................................. C07C 99/12
[52] U.S. Cl. .................... 562/443; 562/442; 562/553; 562/562; 562/554; 562/556; 562/559; 562/560; 562/563; 562/561; 548/496; 548/344; 548/572; 260/502.4 R
[58] Field of Search ................ 260/502.4 R; 560/445, 560/453, 462, 443, 463, 553, 554, 556, 551, 560, 563, 561; 548/572, 344, 496

[56] References Cited

U.S. PATENT DOCUMENTS

| | | | |
|---|---|---|---|
| 2,681,927 | 6/1954 | McCollum et al. | 562/562 |
| 2,751,408 | 6/1956 | Hoglan et al. | 562/445 |
| 2,894,954 | 7/1959 | Dewitt et al. | 562/445 |
| 2,949,450 | 8/1960 | Stark | 562/445 |
| 4,464,498 | 8/1984 | Sugiura | 562/445 |

*Primary Examiner*—James H. Reamer
*Attorney, Agent, or Firm*—Frank M. Van Riet

[57] ABSTRACT

A method for the extraction of certain amino acids from aqueous solutions by contacting said solutions with various dithiophosphinates in conjunction with a polar diluent is disclosed.

12 Claims, No Drawings

EXTRACTION OF AMINO ACIDS FROM AQUEOUS SOLUTION WITH DITHIOPHOSPHINATES

BACKGROUND OF THE INVENTION

The production of amino acids, especially by biosynthesis, e.g. fermentation, has become increasingly important in recent years. These amino acids have been found to be useful intermediates in the production of food flavorings and food supplements and also in medical research. U.S. Pat. No. 3,616,224, for example, teaches the synthesis of amino acids from a microorganism of the species Schromobacter methanolphilia or Pseudomonas insueta while U.S. Pat. Nos. 3,660,235 and 3,759,790 culture Brevibacterium, Corynebacterium, Anthrobacter, Bacillus, Candida and others. U.S. Pat. Nos. 3,909,353; 4,016,037 and 4,403,003 also teach methods of amino acid production.

One of the basic problems one faces in the production of amino acids, especially in aqueous media, is the ultimate recovery of the amino acid once its production is complete.

In all of the above-cited U.S. patents, the amino acid product is recovered by means of ion exchange resins, filtration, centrifugation, precipitation at the isoelectric point, activated carbon treatment and the like.

Recently, German Offen. No. 2822870, was published describing the extraction of amino acids from aqueous solutions with a non-aromatic $C_4$–$C_8$ ketone containing cumenesulfonic acid partially neutralized by alkali.

While these techniques for the isolation of amino acids from aqueous solution have proven reasonably successful, the need still exists for means for amino acid recovery wherein increased yields are achieved and/or less expensive extractants are employed.

SUMMARY OF THE INVENTION

It has now been found that amino acids can be extracted from aqueous solutions utilizing extractants comprising various dithiophosphinates whereby many of the difficulties attendant other previously known extractants are avoided. The dithiophosphinates of the present invention are water-insoluble and are therefore easily separated from the extraction extract. They are highly efficient when used in conjunction with diluents and thus, enable the isolation of greater yields of desired amino acid.

DESCRIPTION OF THE INVENTION INCLUDING PREFERRED EMBODIMENTS

In accordance with the invention described herein, amino acids which are present in aqueous solutions are recovered therefrom in more concentrated form. The process comprises contacting an aqueous solution containing a monocarboxylic amino acid free of hydroxy groups with a sufficient amount of a dithiophosphinate having the formula:

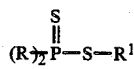

wherein each R, individually, is an alkyl or cycloakyl radical of 4–18 carbon atoms, inclusive, an aryl radical of 6–18 carbon atoms, inclusive, an aralkyl radical of 7–20 carbon atoms, inclusive, or both R's, together with the phosphine atom, from either a 5 or 6 membered ring which may contain oxygen, or a bicyclic radical, and $R^1$ is hydrogen or a cation, in the presence of an organic diluent which forms a substantially water-insoluble liquid when in contact with the dithiophosphinate under the extraction conditions. The extracted solution is then separated from the dithiophosphinate-containing liquid.

Examples of suitable cations include ammonium, alkali metals such as sodium, potassium and the like.

The process of this invention is especially advantageous when applied to the recovery of such amino acids as l-leucine, d-lysine, l-phenylalanine, l-tryptophane, l-histidine, glycine, l-alanine, l-valine, d-norleucine, l-isoleucine, l-cysteine, l-methionine, l-arginine, l-glutamine, di-ornithine, l-proline, mixtures thereof and the like.

Examples of dithiophosphinates useful herein and falling within the scope of the formula set forth above include dicyclohexyldithiophosphinic acid, ammonium bis(2,4,4-trimethylpentyl)dithiophosphinate, bis(α-methylphenethyl)dithiophosphinic acid, ammonium bis(α-methylphenethyl)dithiophosphinate, ammonium diphenyldithiophosphinate, sodium bis(2,4,4-trimethylpentyl)dithiophosphinate, 2,4,6-triisopropyl-1,3-dioxa-5-phosphacyclohexane-5-dithioic acid ammonium salt; 9-phospha-bicyclo[4.2.1] nonane-dithioic acid and its salts; and the like. The preferred dithiophosphinates are dicyclohexyldithiophosphinic acid (DCPA) and ammonium bis(2,4,4-trimethylpentyl)dithiophosphinate (ATDP).

The above-described dithiophosphinates are employed as solutions in a diluent. The diluent may comprise any organic material which results in a substantially water-insoluble liquid when in contact with the dithiophosphinate extractant under the extraction conditions. Suitable diluents include long chain alcohols such as octanol, tridecyl alcohol, decanol, etc.; methyl isobutylketone; liquid mixtures of phosphine oxides such as 70 wt. percent tri-n hexyl and 30 wt. percent tri-n-octyl phosphine oxides; di-n-butylsulfoxide; di-n-propyl sulfone; and the like.

The aqueous amino acid solution should be contacted with the dithiophosphinate exctractant at a pH in the range of from about 1–9, preferably from about 2–6 and at a temperature ranging from about 5°–80° C., preferably room temperature to about 60° C. in order to obtain optimum results.

The aqueous amino acid solution is contacted via a liquid-liquid extraction, either batch or continuously countercurrent with the solution of diluent and dithiophosphinate A ratio of aqueous (A) phase to organic (O) phase is chosen to most efficiently remove the amino acid from solution, it being preferred to use as high a concentration of dithiophosphinate in the diluent as possible.

The dithiophosphinate-diluent may be used as such or supported on a solid carrier or support. Usually the support is inert, however, it is also permissible to use chemically active supports without falling outside the scope of the present invention.

The solid materials or supports for the extractants of the present invention are preferably water-insoluble adsorbents and include, but are not limited to, such materials as diatomaceous earth, silica, wide-pore carbon, and the like, or crosslinked polymer materials in the form of porous beads. Synthetic macroporous, crosslinked copolymers of styrene and divinyl benzene are commonly used support materals. Other commonly used supports are, for example, divinylbenzene crosslinked polyacrylates and polymethacrylates. These supports themselves are generally not critical and a convenient support amenable to a particular application may easily be determined by one skilled in the art with simple experimentation.

Many monovinyl compounds (monomers) can be used alone or combined in the preparation of the polymeric supports useful in the present invention. They include, but are not limited to, styrene, methylstyrene, acrylic acid, methacrylic acid, acrylonitrile, vinyl anisole, vinyl naphthalene; acrylic and methacrylic acid esters, such as methylethyl, propyl-, isopropyl-, butyl-, isobutyl-, tert.butyl-, ethyl-, hexyl-, cyclohexyl-, benzyl-, phenylethoxymethyl, propoxymethyl-, propoxypropyl-, ethoxyphenyl-, ethoxybenzyl-, ethoxycyclohexyl-, methoxycyclohexyl acrylates and methacrylates; alkylphenyl acrylates and methacrylates; ethylene, propylene, isobutylene, diisobutylene; vinyl chloride; vinyl acetate, vinylidene chloride, and the like. Polyethylenically unsaturated monomers, such as butadiene, isoprene, chloroprene, which behave as if they had only a simple double bond, are also suitable.

Suitable polyvinyl compounds which function as crosslinking agents include, but are not limited to, divinylbenzene, divinylpyridine, divinyltolene, divinylnaphthalene, diallyl phthalate, divinylxylene, divinylethylbenzene, divinylsulfone, polyvinyl or polyallyl ethers of glycols, glycerine and pentaerythritol, divinylketone, divinyl sulfide, allylacrylate, diallylmaleate, diallylfumarate, diallyl succinate, diallyl carbonate, diallyl malonate, diallyl oxalate, diallyl adipate, diallyl sebacate, divinyl sebacate, diallyl silicate, triallyl phosphate, N,N'-methylenediacrylamide, N,N'-methylenedimethacrylamide, N,N'-ethylenediacrylamide, trivinylbenzene, trivinylnaphthalene, and the like. The amount of polyvinyl compound used may vary over wide limits. In general, however, the polyvinyl compound is used in an amount ranging from about 5 to 70% by weight, based on the total weight of monomers, and preferably between about 8 and 60% by weight.

The extractant may be incorporated in or on the support material by any convenient technique. Conventional and applicable techniques include, but are not limited to, impregnation, with the aid of a solvent, or by encapsulation, through the addition of the extractant to the monomer mixture, adding a polymerization catalyst, and then polymerizing the resulting mixture or solution of monomers in the presence of the extractant by conventional techniques. A procedure for the encapsulation of extractants via this technique is described by Krobel et al, U.S. Pat. No. 3,960,762.

In addition to the polymeric crosslinked macroporous polymers described above, the present invention may utilize as the polymeric support material crosslinked macroporous copolymers containing dithiophosphinate functions directly bonded to the polymer backbone, see, for example, European Patent Application No. 0031761 to Bolleau et al. Similar polymers are described by McKinley et al, U.S. Pat. No. 3,708,462.

The amount of dithiophosphinate-diluent incorporated in or on the support material by impregnation or encapsulation, or by the use of polymers, may vary over wide limits, provided sufficient dithiophosphinate is available to extract the amino acids from solutions containing them. Ordinarily, the need for efficiency of extraction will determine the amount of extractant used and these levels can be easily determined by the skilled artisan by sample experimentation.

Liquid membrane extraction as described by Bock, Valint and Hayworth of Exxon Research and Engineering Company and selective supported membrane extraction as described by Obermayer, Nichols, Allen and Caron of the Moleculon Research Corporation may also be used.

The amino acid may be ultimately isolated by stripping from the dithiophosphinate-diluent extractant by washing with any suitable solvent such as water, salts such as aqueous ammonium sulfate, aqueous ammonium chloride or the like.

The following examples are set forth for purposes of illustration only and are not to be construed as limitations on the present invention except as set forth in the appended claims. All parts and percentages are by weight unless otherwise specified.

In the following examples, analysis of the aqueous phase is accomplished by either acid titration or liquid chromatography. Organic phase loading is determined by difference.

1. Titration:

Non-specific acid titration of amino acids involves addition of excess formaldehyde to the sample and titrating with sodium hydroxide to the weak acid end point. Formaldehyde forms methylolamine, so that the resulting compound is more acidic than the free amino acid.

2. Liquid Chromatography:

A Hamilton PRP-1 organic reversed phase column is used with a $Na_2HPO_4$—$H_3PO_4$ buffer at pH 3. Detection is by UV (254 nm). The method gives a material balance when both the aqueous and organic phases are assayed.

EXAMPLES 1 AND 2

Two media formulations are prepared according to the following recipes to give broths A and B.

| Broth A | | Broth B | |
|---|---|---|---|
| $K_2HPO_4$ | .75 g | $KH_2PO_4$ | 1.5 g |
| $KH_2PO_4$ | .75 g | $MgSO_4.7H_2O$ | 0.6 g |
| $MgSO_4.7H_2O$ | .375 g | $(NH_4)_2SO_4$ | 67.5 g |
| $(NH_4)_2SO_4$ | 30.0 g | Hydrolyzed soybean protein | 37.5 g |
| Cornsteep liquor | 7.5 g | | |
| $CaCO_3$ | 30.0 g | $CaCO_3$ | 75.0 g |
| deion. water | 1200 ml | $FeSO_4$ | 3.0 mg |
| | | $MnCl_2.7H_2O$ | 3.0 mg |
| | | d-biotin | 75 µg |
| | | thiamine | 300 µg |
| | | deion. water | 1200 ml |

Each broth is adjusted to pH 7.2 with 50% aqueous KOH. Forty mls. of each broth are then dispensed to a suitable culture flask, capped and autoclaved for 15 minutes at 121° C. After cooling, 10 ml of 50% glucose (w/v) is added to each vessel. The vessels are then inoculated with l-phenylalanine producing culture and incubated. Mutant bacteria belonging to the corgnebacterium glutamicium are used in accordance with U.S. Pat. No. 3,759,790, Example 1. By liquid chromatographic analysis, broth A contains 0.23 weight percent l-phenylalanine (lPA) and broth B contains 0.18 weight percent.

Each broth is then contacted with 283 parts/L of ammonium bis(2,4,4-trimethylpentyl)dithiophosphinate in decanol at A/O=1. The broths are stirred for 15 minutes at room temperature. Analysis of the resultant aqueous phases shows 82% extraction of 1PA from broth A and 71% extraction of 1PA from broth B.

EXAMPLES 3-34

To a suitable reaction vessel is charged a 2.5 wt. percent aqueous solution of 1-phenylalanine (1PA) and a diluent solution of a dithiophosphinate. The vessel is sealed and the contents stirred at 25° C. for 15 minutes. In each instance, the pH is adjusted appropriately, the dithiophosphinate and diluent being varied. The results are set forth in Table I, below.

TABLE I

| Ex. | Conc-pts/L | Diluent | A/O | pH | % 1PA extracted | Assay Method |
|---|---|---|---|---|---|---|
| Decanol Only | | | | | | |
| 3C | neat | — | 1.0 | 6.7 | 0.8 | l.c. |
| 4C | neat | — | 0.3 | 6.2 | 1.0 | l.c. |
| 5C | neat | — | 1.0 | 3.0 | 2.1 | l.c. |
| Dicyclohexyldithiophosphinic Acid | | | | | | |
| 6C | 20 | Exxon 150 | 0.3 | 3.8 | 1 | t. |
| 7C | 50 | decalin | 0.36 | 3.5 | 0* | l.c. |
| 8C | 50 | DIBK | 0.3 | 2.8 | 0 | l.c. |
| 9 | 50 | MIBK | 0.3 | 2.6 | 31 | l.c. |
| 10 | 50 | LPO | 0.3 | 2.7 | 88* | t. |
| 11 | 50 | decanol | 0.1 | 3.1 | 88* | t. |
| 12 | 50 | " | 0.3 | 1.6 | 34* | t. |
| 13 | 50 | " | 0.3 | 2.4 | 83* | t. |
| 14 | 50 | " | 0.3 | 3.6 | 83* | l.c. |
| 15 | 50 | " | 1.0 | 2.8 | 63* | l.c. |
| 16 | 80 | " | 1.0 | 2.6 | 69** | l.c. |
| 17 | 80 | " | 2.0 | 2.8 | 42** | l.c. |
| 18 | 80 | " | 3.0 | 2.7 | 31** | l.c. |
| Ammonium bis(2,4,4-trimethylpentyl)dithiophosphinate | | | | | | |
| 19 | 50 | decanol | 0.3 | 2.6 | 78 | l.c. |
| 20 | 165 | " | 1.0 | 2.9 | 76 | l.c. |
| 21 | 165 | " | 1.0 | 1.8 | 58 | l.c. |
| 22 | 165 | " | 1.0 | 1.3 | 40 | l.c. |
| 23 | 300 | " | 1.0 | 2.3 | 74 | l.c. |
| 24 | 300 | " | 1.0 | 4.8 | 82 | l.c. |
| 25C | 82 | DIBK | 1 | 3.3 | 1 | l.c. |
| 26 | 108 | MIBK | 1 | 3.1 | 18 | l.c. |
| 27 | 137 | Di—n-butyl sulfoxide | 1 | 3.2 | 67 | l.c. |
| 28 | 87 | Di—n-propyl sulfone | 1 | 3.2 | 49 | l.c. |
| 29 | 165 | Tridecanol | 1 | 3.1 | 62 | l.c. |
| MIBK Only | | | | | | |
| 30C | neat | — | 1.0 | 2.9 | 2 | l.c. |
| Di—n-butyl sulfoxide Only | | | | | | |
| 31C | neat | — | 1.0 | 3.3 | 24 | l.c. |
| Di—n-propyl sulfone Only | | | | | | |
| 32C | neat | — | 1.0 | 3.1 | 3 | l.c. |
| Tridecanol Only | | | | | | |
| 33C | neat | — | 1.0 | 3.0 | 0 | l.c. |
| Sodium bis(2,4,4-trimethylpentyl)dithiophosphinate | | | | | | |
| 34 | 143 | decanol | 0.3 | 3.1 | 80 | l.c. |

C = comparative
Exxon 150 = 97 vol. % arom. hydrocarbon of 70 vol. % $C_{10}$-$C_{11}$ compounds
MIBK = methylisobutyl ketone
DIBK = diisobutyl ketone
LPO = liquid mixture containing 70 wt. % tri-n-hexyl and 30 wt. % tri-n-octyl phosphine oxide
l.c. — liquid chromatography
t. = titration
* = extraction at 55° C.
** = titration gave 54; 32; and 10, resp.

EXAMPLES 35-48

Following the procedure of Example 11 various dithiophosphinates are used in decanol to extract the 1PA solution at 25° C. The results are set forth in Table II, below.

TABLE II

| Ex. | Conc. pts/L | A/O | pH | % 1PA Extracted | Assay Method |
|---|---|---|---|---|---|
| 35 | 50 | 0.3 | 4.4 | 75 | t. |
| 36 | 150 | 1.0 | 1.4 | 27 | t. |
| 37 | 150 | 1.0 | 2.2 | 63 | t. |
| Bis(α-methylphenethyl)dithiophosphinic acid ammonium salt | | | | | |
| 38 | 250 | 1.0 | 1.6 | 56 | l.c. |
| 39 | 250 | 1.0 | 3.0 | 84 | l.c. |
| 40 | 250 | 1.0 | 5.0 | 64; 63 | l.c.; t. |
| 2,4,6-triisopropyl-1,3-dioxa-5-phosphacyclohexane-5-dithioic acid ammonium salt | | | | | |
| 41 | 200 | 1.0 | 6.5 | 36 | l.c. |
| 42 | 200 | 1.0 | 1.5 | 80 | l.c. |
| 9-phosphabicyclo[4.2.1]nonane dithioic acid | | | | | |
| 43 | 50 | 0.3 | 2.5 | 96 | l.c. |
| 44 | 50 | 0.3 | 3.0 | 92 | l.c. |
| 9-phosphabicyclo[4.2.1]nonane dithioic acid ammonium salt | | | | | |
| 45 | 100 | 1.0 | 6.1 | 12 | l.c. |
| 46 | 100 | 1.0 | 1.3 | 64 | l.c. |
| Diphenyldithiophosphinic Acid ammonium salt | | | | | |
| 47 | 63 | 0.3 | 3.3 | 84 | l.c. |
| Dilauryldithiophosphinic Acid ammonium salt | | | | | |
| 48 | 200 | 1.0 | 2.9 | 78 | l.c. |

EXAMPLES 49-72 (comparative)

The procedure of Example 11 is again followed except that various extractants falling outside the scope of the present invention are employed. The results are set forth in Table III, using titration analysis.

TABLE III

| Ex. | Conc. pts/L | Diluent | A/O | pH | % 1PA Extracted |
|---|---|---|---|---|---|
| 49 | 146 | decanol | 0.5 | 0.4 | 20 |
| 50 | 146 | " | 0.5 | 0.5 | 13* |
| 51 | 150 | " | 0.5 | 2.5 | 6 |
| Dicyclohexylphosphinic acid | | | | | |
| 52 | 80 | decanol | 0.3 | 3.8 | 13 |
| 53 | 300 | " | 0.3 | 2.4 | 10 |
| 54 | 300 | " | 1.0 | 6.8 | 0 |
| 55 | 150 | Exxon 150 | 0.3 | 7.8 | 0 |
| 56 | 150 | " | 0.3 | 2.5 | 0 |
| Tri-n-octyl phosphine oxide | | | | | |
| 57 | 300 | Exxon 150 | 0.3 | 2.4 | 0 |
| 58 | 300 | " | 0.3 | 3.6 | $0^2$ |
| 59 | 300 | " | 0.3 | 4.8 | 0 |
| 60 | 300 | " | 0.3 | 2.0 | 0 |
| 61 | 300 | " | 0.3 | 1.5 | 0 |
| 62 | 300 | " | 0.3 | 1.0 | 0 |
| 63 | 300 | " | 0.5 | 5.9 | 0 |
| 64 | 165 | Decanol | 0.3 | 3.1 | $0^3$ |
| LPO | | | | | |
| 65 | 870 | — | 1.0 | 4.0 | $0^3$ |
| 66 | 870 | — | 1.0 | 1.8 | $0^3$ |
| Tri-n-octylphosphine sulfide | | | | | |
| 67 | 300 | Exxon 150 | 0.3 | 0.6 | 0 |
| 68 | 300 | " | 0.3 | 1.2 | 0 |
| 69 | 300 | " | 0.3 | 1.6 | 0 |
| 70 | 300 | " | 0.3 | 7.2 | 0 |
| 71 | 165 | Decanol | 0.3 | 3.2 | $4^3$ |
| Bis(2,4,4-trimethylpentyl)thiophosphinic Acid Ammonium Salt | | | | | |
| 72 | 47 | Decanol | 0.3 | 3.1 | $0^3$ |

* = extraction at 50° C.
$^2$ = 0.6 wt. % $CH_2O$ present
$^3$ = liquid chromatography used.

EXAMPLES 73-76

The procedure of Example 11 is again followed to extract various amino acids from solution. Dicyclohexyldithiophosphinic acid in decanol is used as the extractant. The assay is by titration. The results are set forth in Table III, below.

TABLE III

| Ex. | α-Amino Acid | Conc. wt. % | A/O | pH | % Amino Acid Extracted |
|---|---|---|---|---|---|
| 73 | 1-Leucine | 2.1 | 0.3 | 2.9 | 82 |
| 74 | 1-Lysine | 2.3 | 0.3 | 3.5 | 60 |
| 75C | 1-Threonine | 2.5 | 0.3 | 3.0 | 0 |
| 76C | Glutamic Acid | 0.7 | 0.3 | 2.7 | 0 |

EXAMPLES 77–82

Following the procedure of Example 11, the following various dithiophosphinates of Formula I are used in decanol to extract the 1PA solution at 25° C. Similar results are obtained.

Example 77

Distearyl dithiophosphinate, potassium salt.

Example 78

Dinaphthyl dithiophosphinate, sodium salt.

Example 79

Dibenzyl dithiophosphinate, ammonium salt.

Example 80

Bis(4-octylbenzyl)dithiophosphinic acid.

Example 81

Bis(octylnaphthyl)dithiophosphinic acid, sodium salt.

Example 82

Bis(2,4,4-trimethylpentyl)dithiophosphinic acid.

We claim:

1. A method for recovering monocarboxylic amino acids free of hydroxy groups from aqueous solutions thereof which comprises contacting such a solution with a sufficient amount of a dithiophosphinate having the formula:

wherein each R, individually, is an alkyl or cycloalkyl radical of 4–18 carbon atoms, inclusive, an aryl radical of 6–18 carbon atoms, inclusive, an aralkyl radical of 7–20 carbon atoms, inclusive, or both Rs, together with the phosphine atoms, form either a 5 or 6 membered ring which may contain oxygen, or a bicyclic radical, and $R^1$ is hydrogen or a cation, in the presence of an organic diluent which forms a substantially water-insoluble liquid when in contact with the dithiophosphinate under extraction conditions to extract said amino acid and separating the extracted solution from said dithiophosphinate.

2. A method according to claim 1 wherein said dithiophosphinate is dicyclohexyldithiophosphinic acid.

3. A method according to claim 1 wherein said dithiophosphinate is ammonium bis(2,4,4-trimethylpentyl)dithiophosphinate.

4. A method according to claim 1 wherein said diluent is decanol.

5. A method according to claim 1 wherein said amino acid is 1-phenylalanine.

6. A method according to claim 1 wherein said diluent is a liquid phosphine oxide mixture.

7. A method according to claim 1 wherein said dithiophosphinate is 9-phosphabicyclo[4.2.1]nonane dithioic acid.

8. A method according to claim 1 wherein said dithiophosphinate and diluent are employed on a solid support therefor.

9. A method according to claim 1 wherein said solution is a product of fermentation.

10. A method according to claim 1 wherein said dithiophosphinate is diphenyldithiophosphinic acid.

11. A method according to claim 1 wherein said dithiophosphinate is bis(2,4,4-trimethylpentyl)dithiophosphinic acid.

12. A method according to claim 1 wherein said dithiophosphinate is 2,4,6-triisopropyl-1,3-dioxa-5-phosphacyclohexane-5-dithioic acid ammonium salt.

* * * * *